US012678321B2

(12) United States Patent
Yilmaz

(10) Patent No.: US 12,678,321 B2
(45) Date of Patent: Jul. 14, 2026

(54) APPARATUS AND METHOD FOR POSITIONING A BODY PART

(71) Applicant: MedikEquip LLC, Seattle, WA (US)

(72) Inventor: Hakan Yilmaz, Fircrest, WA (US)

(73) Assignee: MedikEquip LLC, Seattle, WA (US)

( * ) Notice: Subject to any disclaimer, the term of this patent is extended or adjusted under 35 U.S.C. 154(b) by 25 days.

(21) Appl. No.: 18/785,399

(22) Filed: Jul. 26, 2024

(65) Prior Publication Data

US 2024/0382335 A1     Nov. 21, 2024

Related U.S. Application Data

(62) Division of application No. 17/394,876, filed on Aug. 5, 2021, now Pat. No. 12,070,409.

(51) Int. Cl.
| | |
|---|---|
| *A61F 5/37* | (2006.01) |
| *A61G 13/12* | (2006.01) |

(52) U.S. Cl.
CPC ........ *A61F 5/3776* (2013.01); *A61G 13/1245* (2013.01)

(58) Field of Classification Search
CPC ...... A61F 5/04–05; A61F 5/058–05875; A61F 5/37–3792; A61G 13/12; A61G 13/1205; A61G 13/123–125; A61G 13/128; A61G 13/1285; A61G 13/0081; A61H 1/0237–0288; A61H 2001/0203
USPC ........................................... 128/845
See application file for complete search history.

(56) References Cited

U.S. PATENT DOCUMENTS

| | | | | |
|---|---|---|---|---|
| 1,976,244 | A | * | 10/1934 | Moran ................... A61F 5/3753 |
| | | | | 602/20 |
| 3,027,895 | A | * | 4/1962 | Williams .............. A61F 5/3761 |
| | | | | 128/878 |
| 4,526,165 | A | * | 7/1985 | Mielnik, Jr. ........... A61G 13/12 |
| | | | | 128/882 |
| 4,549,540 | A | * | 10/1985 | Caspari ................. A61F 5/3761 |
| | | | | 128/882 |
| 4,576,151 | A | * | 3/1986 | Carmichael ........... A61F 5/0193 |
| | | | | 602/24 |
| 6,241,215 | B1 | | 6/2001 | Gersemsky et al. |
| 6,467,106 | B1 | | 10/2002 | Heimbrock |
| 10,849,806 | B2 | | 12/2020 | Yilmaz |
| 11,058,594 | B2 | | 7/2021 | Yilmaz |
| 2003/0045818 | A1 | * | 3/2003 | Huang ................. A61H 1/0237 |
| | | | | 601/97 |
| 2004/0050391 | A1 | * | 3/2004 | Kiwala ................. A61F 5/3715 |
| | | | | 128/882 |

(Continued)

FOREIGN PATENT DOCUMENTS

| | | | | |
|---|---|---|---|---|
| WO | WO 00/62721 | * | 10/2000 | ............... A61F 5/04 |

*Primary Examiner* — Adam Baker
(74) *Attorney, Agent, or Firm* — Foley & Lardner LLP

(57) ABSTRACT

Apparatus and methods for positioning a body part of a patient. An apparatus can comprise a portable support structure configured to be placed on a patient support surface under a body part of a patient and retention elements attached to the support structure. At least a portion of the support structure is configured to move from lowered position to a raised position above the lowered position. The retention elements are configured to receive the body part. Each retention element has a holding portion and an open region, and each retention element faces at least partially sideways in a retention position.

17 Claims, 10 Drawing Sheets

(56)         References Cited

U.S. PATENT DOCUMENTS

| | | | |
|---|---|---|---|
| 2007/0000500 A1* | 1/2007 | Richard | A61F 5/3715 |
| | | | 128/845 |
| 2016/0346147 A1* | 12/2016 | Brown | A61F 5/3769 |
| 2019/0240096 A1 | 8/2019 | Yilmaz | |

* cited by examiner

100

150          154          150

152          152

110

100

150     154          154     150

152          152

L0 ←                              → L0

R

110

100          150          150

152     152

154          154

110

APPARATUS AND METHOD FOR POSITIONING A BODY PART

CROSS-REFERENCE TO RELATED APPLICATION

This application is a divisional of U.S. patent application Ser. No. 17/394,876, now U.S. Patent Application Publication No. 2023/0040567, filed Aug. 5, 2021, the disclosure of which is incorporated by reference herein in its entirety.

TECHNICAL FIELD

The present technology is directed to apparatus and methods for positioning a body part to assist in medical procedures in which movement of the body part can interfere with carrying out the procedure, such as urinary catheterization.

BACKGROUND

Many people undergo urinary catheterization to drain urine, such as when they are incontinent or otherwise cannot urinate on their own. For example, patients undergoing certain types of surgeries (e.g., prostate gland, hip fracture, hysterectomies, etc.) or patients who have certain conditions (e.g., kidney stones, blood clots in the urine, enlargement of the prostate, spinal cord injury, dementia, etc.) are often unable to urinate on their own. Additionally, medications that impair bladder function can cause urine to remain in the bladder. Many people also undergo urinary catheterization to collect urine in certain medical procedures, such as treating kidney diseases or acute decompensated heart failure. To empty the bladder or otherwise collect urine, a patient often undergoes urinary catheterization using an indwelling or intermittent catheter.

Typical urinary catheterization procedures involve inserting a tubular catheter with an open lumen into the bladder through the urethra. Indwelling catheters can be held in place for extended periods of time using a Foley-type catheter with a balloon at the end that is inflated to prevent the tube from sliding out of the urinary tract. Intermittent catheters are often a simple tube configured to be inserted into the bladder through the urinary tract. Either type of urinary catheter can be uncomfortable, and particularly during insertion or extraction through the urinary tract and/or the bladder sphincter.

One drawback of either type of urinary catheter is that patients are often apprehensive about having a catheter inserted through their urinary tract and bladder sphincter. Patients, in fact, may violently struggle against nurses and other medical care professionals during catheter insertion. This is particularly the case for patients who are suffering from dementia, under the influence of various drugs, or are obese. When patients struggle against the caretaker, it generally requires four physically able individuals to restrain the patient during insertion and may require restraining straps. If restraining straps are required, it is necessary to first obtain doctor's orders. Conventional practices requiring such constraint of violent or uncontrollable patients can be time consuming because of the need to organize personnel and obtain a doctor's orders, dangerous to hospital/clinical staff, and expensive in light of the number of personnel involved. Therefore, a need exists to assist nurses and other healthcare professionals in procedures in which certain types of patient movement can interfere with carrying out the procedure.

BRIEF DESCRIPTION OF THE DRAWINGS

Many aspects of the present disclosure can be better understood with reference to the following drawings. The components in the drawings are not necessarily to scale, and instead emphasis is placed on illustrating clearly the principles of the present disclosure. For ease of reference, throughout this disclosure identical reference numbers and/or letters are used to identify similar or analogous components or features, but the use of the same reference number does not imply that the parts should be construed to be identical. Indeed, in many examples described herein, identically numbered components refer to different embodiments that are distinct in structure and/or function. Any headings provided herein are for convenience only.

DETAILED DESCRIPTION

Overview

The present technology is directed to stabilizing patients during a procedure, such as at least partially immobilizing a patient's legs during urinary catheterization. Several embodiments are apparatus for positioning a body part, such as a limb (e.g., legs), comprising a portable support structure configured to be placed on a patient support surface (e.g., a bed or table) under the body part. At least a portion of the support structure is configured to move from a lowered position to a raised position above the lowered position. The apparatus can further include retention elements attached to the support structure and configured to receive the body part. The retention elements have a holding portion and an open region, and the retention elements are moveable to face at least partially sideways in a retention position. In operation, the retention elements at least substantially inhibit the patient from moving the body part in a manner that interferes with the procedure (e.g., substantially immobilize the body part) to thereby stabilize the patient during the procedure. For example, during urinary catheterization, the portable support structure and the retention elements can substantially immobilize the patient's legs in a position in which the practitioner can access the urinary tract without interference from the patient.

Selected Embodiments of Positioning Apparatus

Figure 1A:
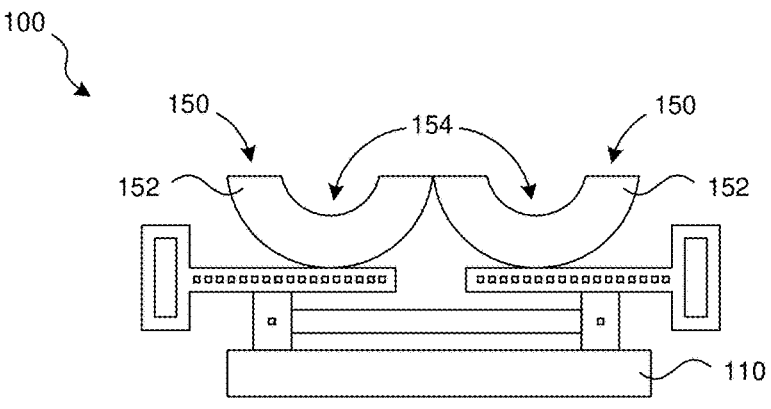
FIGS. 1A-1C are schematic front views of an apparatus in accordance with the present technology.
Figure 1B:
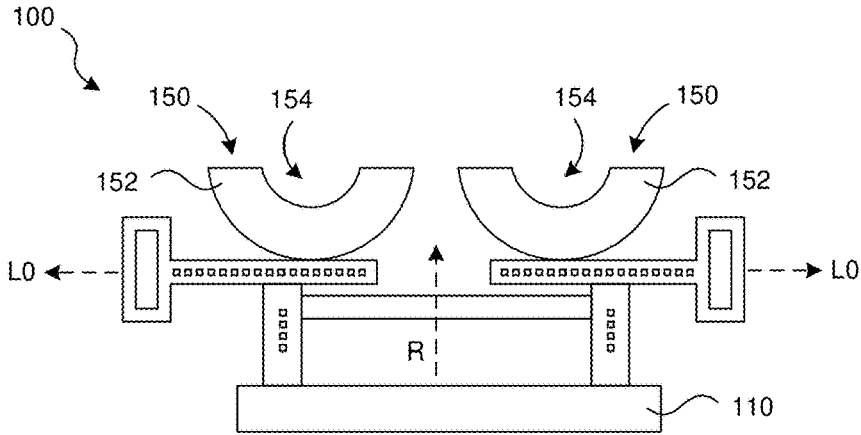
Figure 1C:
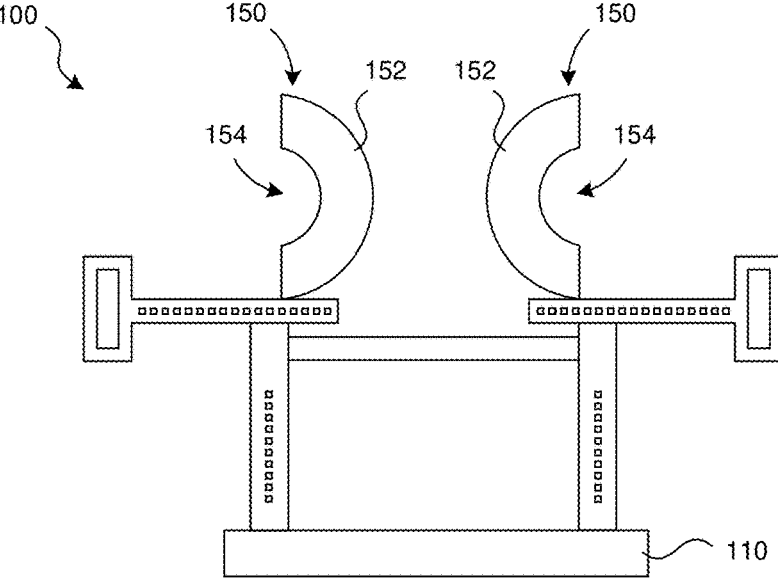

FIGS. 1A-1C are schematic views illustrating a positioning apparatus 100 for position a body part of a patient. The positioning apparatus 100 can include a portable support structure 110 and retention elements 150 attached to the support structure 110. The portable support structure 110 can be configured to be placed on a patient support surface (e.g., a table or bed) under a limb (e.g., a leg) of a patient, and at least a portion of the support structure 110 is configured to move from a lowered position to a raised position for carrying out the procedure (e.g., catheterization). The retention elements 150 are configured to receive the limb of the patient. Each retention element 150 has a holding portion 152 and an open region 154, and the retention elements 150 are configured to move from a receiving position to a retention position.

Referring to FIG. 1A, the support structure 110 is shown in the lowered position and the retention elements 150 are shown in the receiving position in which the open regions 154 of the retention elements 150 face upward. At this stage of operation, the legs of the patient can be placed in the holding portions 152 of the retention elements 150.

FIG. 1B shows the positioning apparatus 100 at an intermediate stage in which the support structure 110 has been raised (arrow R) to an intermediate level and the retention elements 150 have been moved laterally outward (arrows LO). At this stage of operation, the legs of the patient are raised and spread laterally outward compared to the lowered and receiving positions shown in FIG. 1A.

FIG. 1C shows the support structure 110 in the raised position and the retention elements 150 are shown in the retention position in which the open regions 154 of the retention elements 150 face sideways (e.g., laterally outward in this example). The retention elements 150 can be rotated from the receiving position shown in FIG. 1A to the retention position showing in FIG. 1C. At this stage of operation, the legs of the patient are raised and spread laterally outward to immobilize the patient's legs at least substantially during a catheterization procedure. This is expected to significantly reduce the potential for patient interference during urinary catheterization. As a result, the positioning apparatus 100 is expected to reduce complications during urinary catheterization procedures, which is expected to enable practitioners to better care for the patient and avoid further patient discomfort.

Figure 2A:
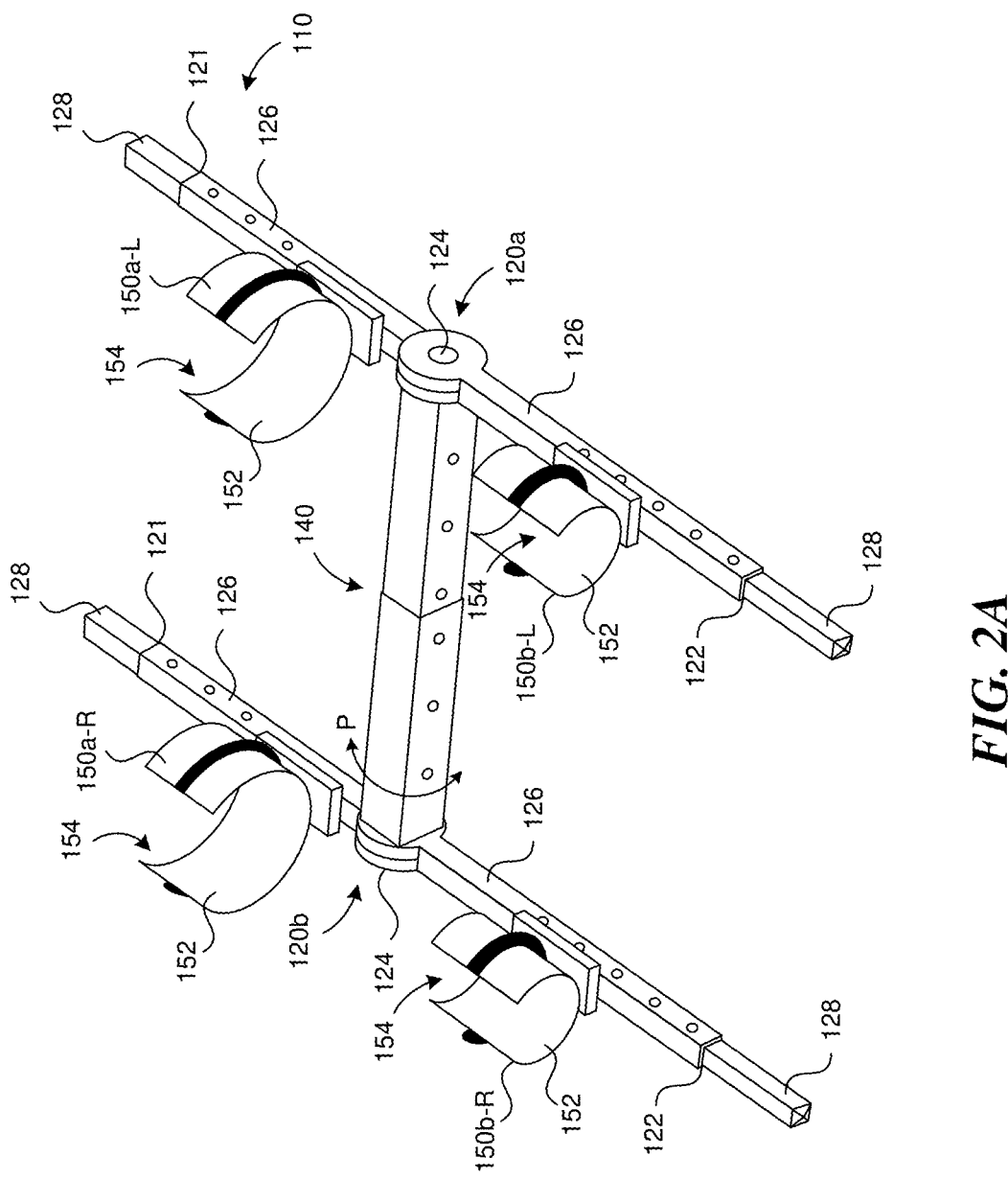
FIGS. 2A and 2B are isometric views.

FIG. 2A is an isometric view of the portable support structure 110 in the lowered position in accordance with some embodiments of the present technology. The support structure 110 can include a left linkage unit 120a, a right linkage unit 120b, and a crossmember 140 coupled to the left linkage unit 120a and the right linkage unit 120b. The left linkage unit 120a and the right linkage unit 120b can each include a first bar 121, a second bar 122 and a rotatable joint 124 coupled to the first bar 121 and the second bar 122. Additionally, each of the first and second bars 121, 122 can include a leg 126 and an extension 128 configured to telescope in/out of the leg 126 to adjust the height of the crossmember 140 relative to the patient support surface. In the lowered position shown in FIG. 2A, the legs 126 of each of the first and second bars 121, 122 can be at least substantially aligned with each other so that the support structure 110 can lay flat on a patient support surface. To configure the support structure in the raised position, the crossmember 140 can be raised such that the legs 126 of the first and second bars 121, 122 rotate about the rotatable joints 124.

Figure 2B:
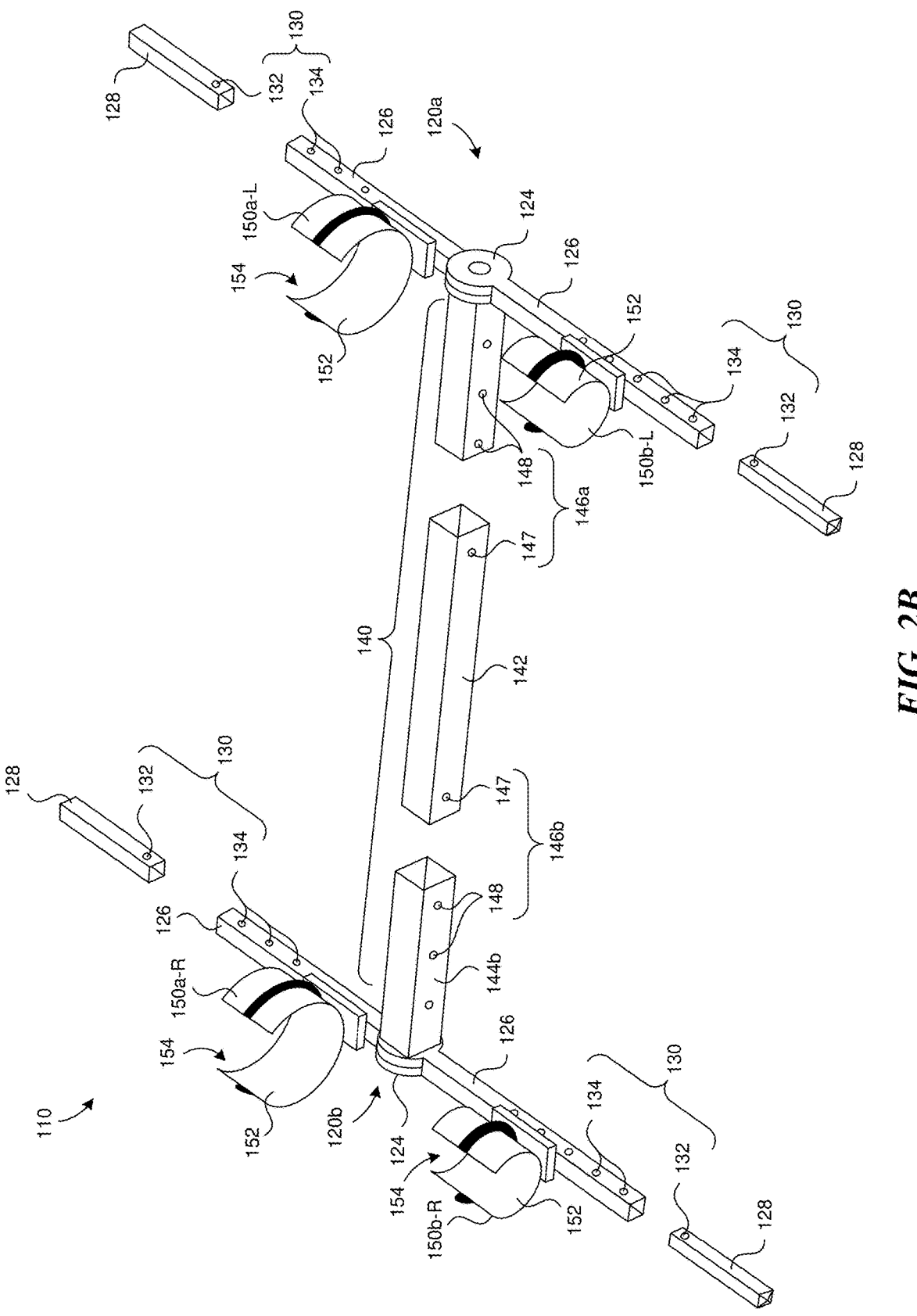

FIG. 2B is an exploded isometric view of the portable support structure 110 in the lowered position in accordance with some embodiments of the present technology. As shown in this view, the support structure 110 can further include locking mechanisms 130 that hold the extensions 128 at various positions relative to the legs 126 to adjust the height of the crossmember 140 in the raised position. Each locking mechanism 130 can include a spring pin 132 on either a leg 126 or a corresponding extension 128 and a series of holes 134 on the other of the leg 126 or corresponding extension 128. In the example shown in FIG. 2B, a spring pin 132 is located at an end of each of the extensions 128 and a series of the holes 134 are located along the legs 126. The extensions 128 can accordingly be positioned relative to the individual legs 126 by depressing the spring pins 132 until the spring pins 132 disengage the holes 134, and then sliding the extensions 128 to the desired position until the spring pins 132 snap into a corresponding hole 134.

The crossmember 140 can further include a crossbar 142, a first connector 144a attached to the rotatable joint 124 of the left linkage unit 120a, and a second connector 144b attached to the rotatable joint 124 of the right linkage unit 120b. The crossmember 140 can include a first locking mechanism 146a and a second locking mechanism 146b, and each of the locking mechanisms can include a spring pin 147 and a series of holes 148 configured to receive the spring pin 147. In the embodiment shown in FIG. 2B, the crossbar 142 has a spring pin 147 at each end, and each of the first and second connectors 144a-b have a series of holes 148 configured to receive the respective spring pins 147 to adjust the lateral distance between the rotatable joint 124 of the left linkage unit 120a and the rotatable joint 124 of the right linkage unit 120b.

Referring to FIGS. 2A-B together, the retention elements 150 can include a left first retention element 150a-L and a left second retention element 150b-L attached to respective legs 126 of the left linkage unit 120a. The retention elements 150 can also include a right first retention element 150a-R and a right second retention element 150b-R attached to respective legs 126 of the right linkage unit 120a. The left and right first retention elements 150a-L and 150a-R can be configured to hold the upper leg (e.g., thigh), and the left and right second retention elements 150b-L and 150b-R can be configured to hold the lower leg (e.g., calf). Each of the retention elements 150 illustrated in FIGS. 2A-B can be a cuff in which the holding portion 152 comprises a curved band configured to extend around a significant portion of the leg and the open region 154 comprises an opening configured to receive the upper or lower leg. In the lowered position shown in FIGS. 2A-B, the open regions 154 face upward to receive the back of the lower leg and the back of the upper leg while a patient is lying down.

Figures 2C, 2D:
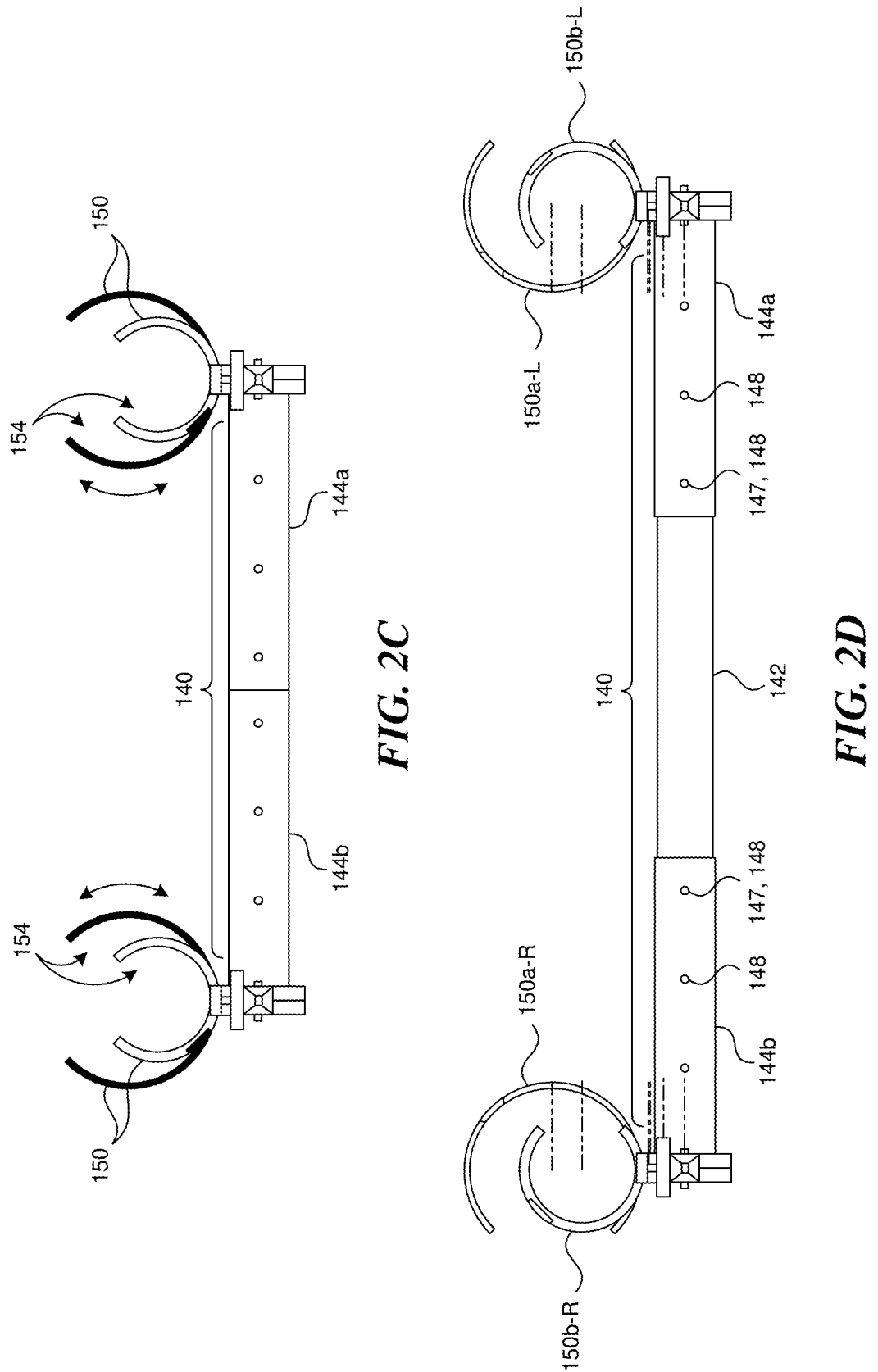
FIGS. 2C and 2D are front views, of an apparatus in accordance with the present technology.

FIGS. 2C and 2D are front views of the portable support structure 110 in accordance with some embodiments of the present technology. FIG. 2C shows the support structure 110 in the lowered position with the retention elements 150 in the receiving position so that the open regions 154 face upward. The connectors 144a-b of the crossmember 140 can be positioned laterally inward as shown in FIG. 2C. FIG. 2D shows the support structure in the lowered position with the open regions 154 of the retention elements 150 facing sideways in the retention position and the first and second connectors 144a-b moved laterally outward to space the left retention elements 150a-L and 150a-R further apart from the right retention elements 150a-R and 150b-R compared to the configuration illustrated in FIG. 2C. In some embodiments as shown in FIG. 2D, the open regions 154 of the left first retention element 150a-L and the right first retention element 150a-R face laterally outward, and the open regions 154 of the left second retention element 150b-L and the right second retention element 150b-R face laterally inward relative to a medial axis of the support structure 110. Conversely, is some embodiments, the open regions 154 of the left first retention element 150a-L and the right first retention element 150a-R face laterally inward, and the open regions 154 of the left second retention element 150b-L and the right second retention element 150*b*-R face laterally outward relative to a medial axis of the support structure 110. In other embodiments, all of the left and right retention elements 150*a*-L, 150*a*-R, 150*b*-L and 150*b*-R can face either laterally inward or laterally outward. Additionally, for cooperative patients who have trouble lifting their legs (e.g., because of injury, age, obesity, etc.), all of the left and right retention elements 150*a*-L, 150*a*-R, 150*b*-L and 150*b*-R can face so that open regions 154 are upward as in FIG. 2C while the first and second connectors 144*a-b* are moved laterally outward as in FIG. 2D.

Figure 3A:
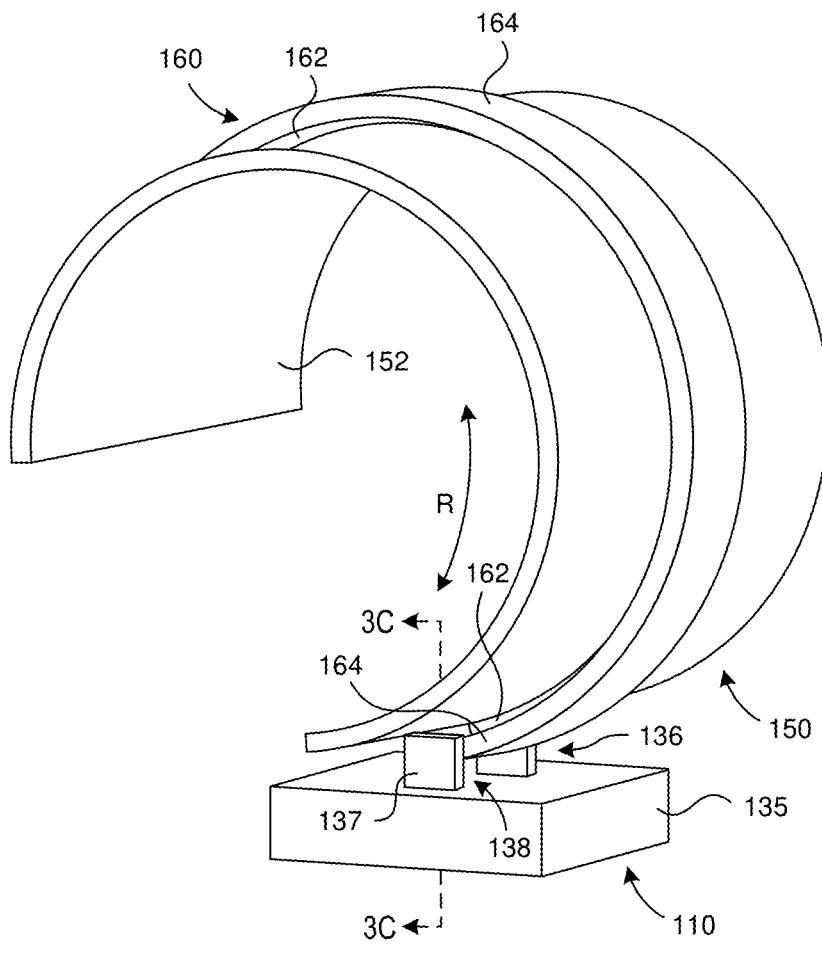
FIG. 3A is an isometric view.
Figure 3B:
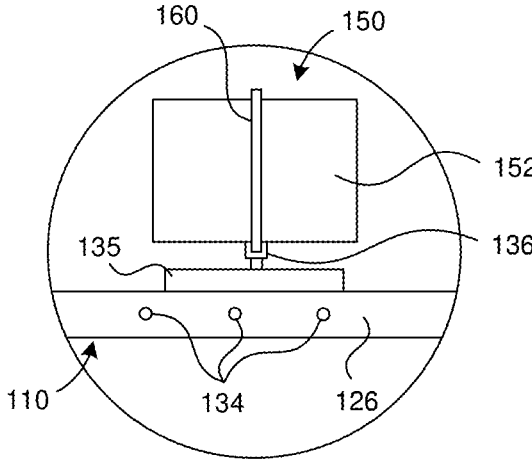
FIG. 3B is a side view.
Figure 3C:
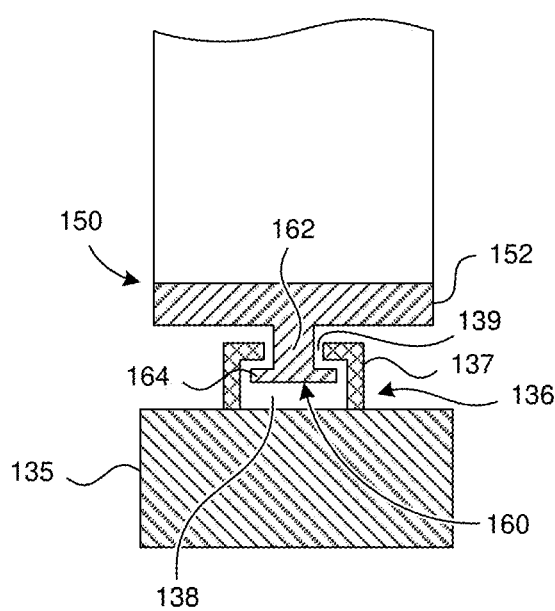
FIG. 3C is a cross-sectional view of a retention element of an apparatus in accordance with the present technology.

FIGS. 3A-3C illustrate an embodiment of the interface between a retention element 150 and the support structure 110 for moving (e.g., rotating) the retention element 150 from the receiving position (FIG. 2C) to the retention position (FIG. 2D). Referring to FIGS. 3A and 3C, the support structure 110 can further include a mount 135 having a retainer 136, and the retention element 150 can further include a connector 160 received in the retainer 136. Referring to FIG. 3B, the mount 135 can be attached to the leg 126 of one of the linkage units 120. Referring to FIG. 3C, the retainer 136 can include a bracket 137 having a channel 138 and a slot 139 extending along the upper portion of the channel 138. The connector 160 can have a base 162 and a flange 164 that extends laterally from the base 162 to form a T-shaped structure. The base 162 extends through the slot 139 and the flange 164 is retained by the lateral portions of the bracket 137 such that the connector 160 can slide through the channel 138 of the retainer 136. Referring to FIG. 3A, for example, the retention element 150 can be rotated (arrow R) relative to the mount 135 such that connector 160 slides through the retainer 136 while the interface between the flange 164 and the lateral portions of the bracket 137 secures the retention element 150 to the support structure 110.

Figure 4A:
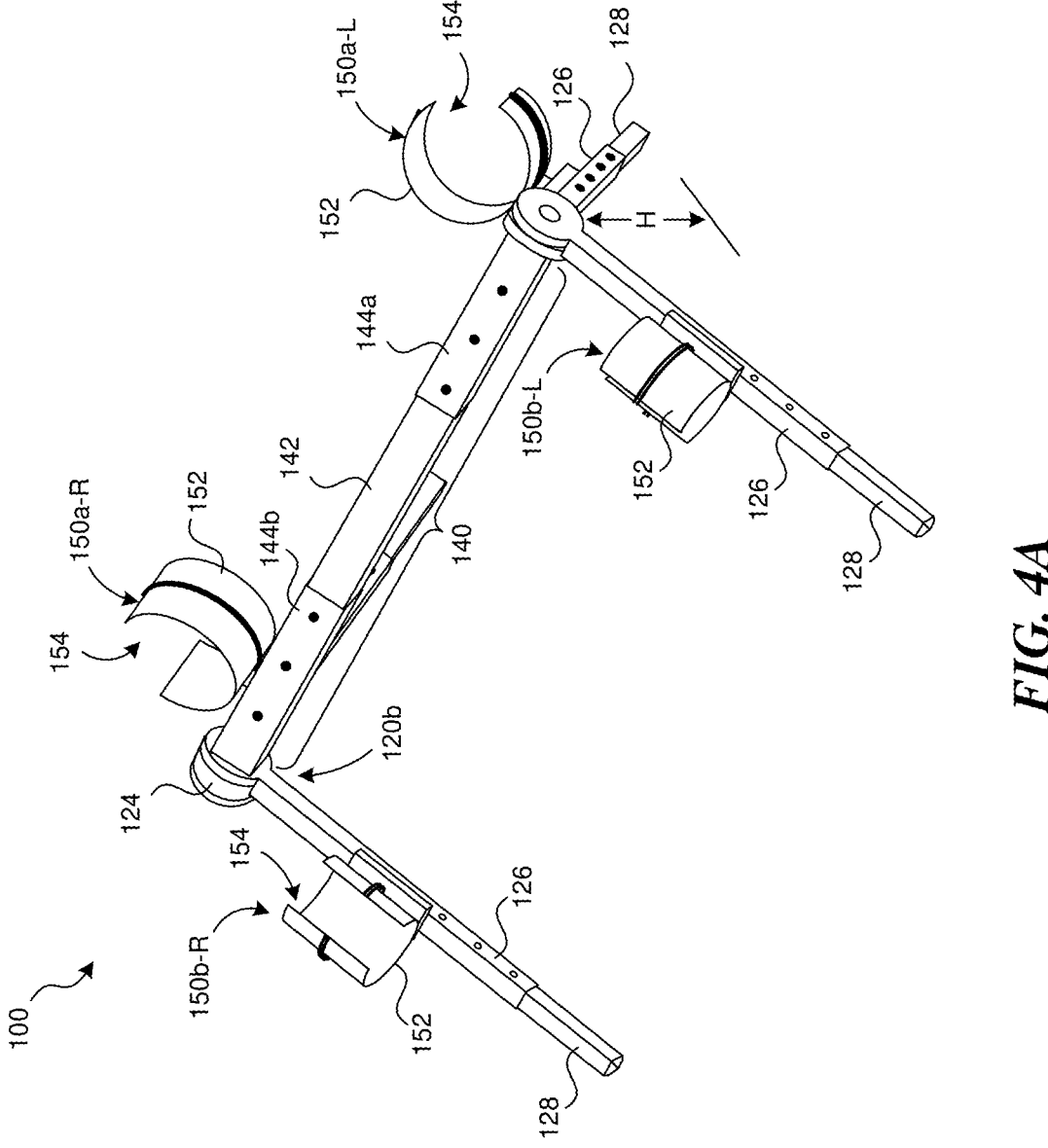
FIG. 4A is an isometric view and FIG. 4B is a front view of an apparatus in accordance with the present technology.
Figure 4B:
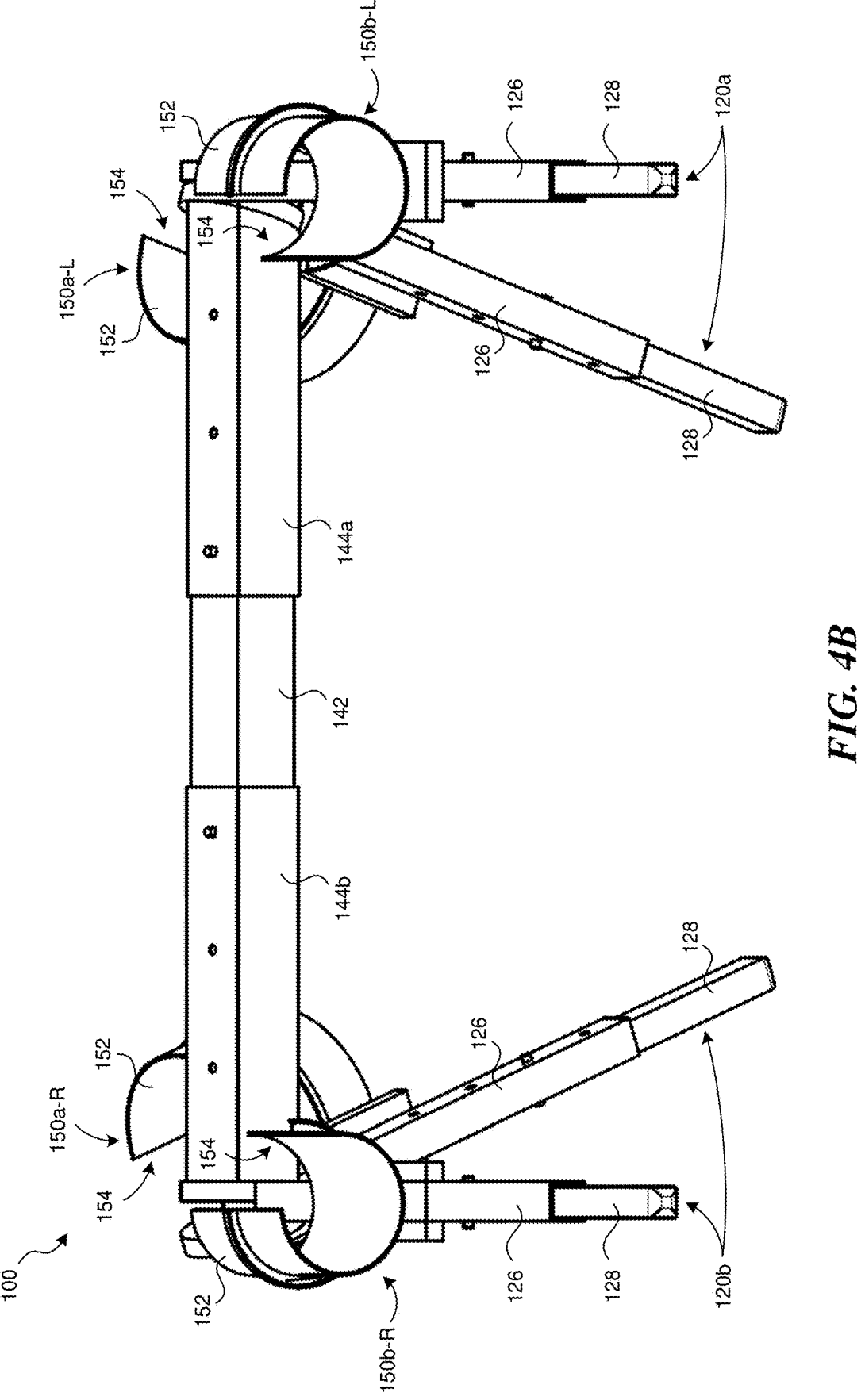

FIGS. 4A and 4B are isometric and front views, respectively, of the positioning apparatus 100 in the raised position. In some embodiments, the positioning apparatus 100 is moved from the lowered position (FIGS. 2A-2D) to the raised position (FIGS. 4A and 4B) by rotating the legs 126 of the left and right linkage units 120*a-b* about their respective joints 124 until the crossmember 140 is at a desired height "H" above the lowered position. Before raising the crossmember 140, the left and right first retention elements 150*a*-L and 150*a*-R can be rotated so that the openings 154 face laterally outward, while the left and right second retention elements 150*b*-L and 150*b*-R can be rotated so that the openings 154 face laterally inward. This secures the upper and lower leg portions in place while the patient is in a more comfortable position. The crossmember 140 can be extended laterally outward by moving the first and second connectors 144*a-b* either before or after raising the crossmember 140 to the raised position.

Once in the raised position shown in FIGS. 4A-B, the positioning apparatus 100 stabilizes (e.g., at least substantially immobilizes) the legs of the patient without having to strap the patient to the bed pursuant to a doctor's order. This is expected to enhance the ability of nurses and other professional caregivers to perform certain procedures in which some patients are likely to move in a manner which would impair the ability of the caregivers to perform the procedures and/or harm or otherwise enhance the discomfort of the patient. For example, the positioning apparatus 100 can be used in urinary catheterization procedures to stabilize the legs of the patient while a caregiver inserts the catheter through the urinary tract to the bladder. Other uses of the positioning apparatus include emergency OB/GYN procedures or other procedures involving genitalia.

Figure 5:
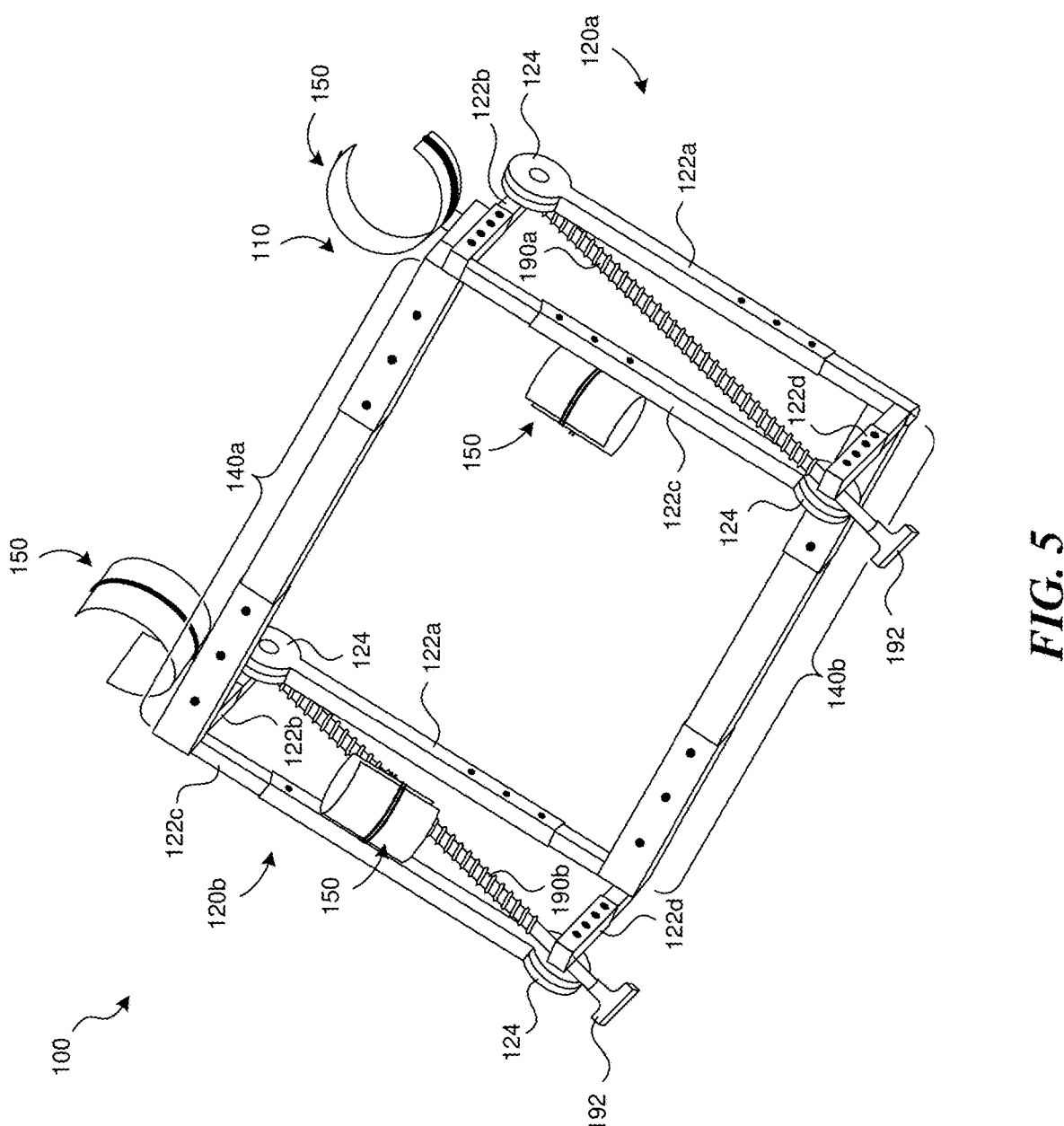
FIG. 5 is a sideview of an apparatus in accordance with the present technology.

FIG. 5 is an isometric view of the positioning apparatus 100 in accordance with some embodiments of the present technology. Several features of the positioning apparatus 100 illustrated in FIGS. 2A-4B are similar to or the same as those in the positioning apparatus 100 illustrated in FIG. 5. For example, the positioning apparatus 100 in all these figures can include retention elements 150 and crossmembers 140 that are similar to or the same as each other. The difference between the positioning apparatus 100 illustrated in FIG. 5 and those described above with reference to FIGS. 2A-4B is that the positioning apparatus 100 illustrated in FIG. 5 has four-bar left and right linkage units 120*a-b*, respectively, an upper crossmember 140*a*, and a lower crossmember 140*b*. In this embodiment, for example, each of the left and right linkage units 120*a-b* can have four bars 122*a-d*, and each of the bars 122*a-d* can have one end rotatably coupled to one of the upper crossmember 140*a* or the lower crossmember 140*b* and an opposing end rotatably coupled to a joint 124. The upper and lower crossmembers 140*a-b* can have a crossbar and connectors as described above with reference to the crossmember 140 of FIGS. 2A-4B. Additionally, the left linkage unit 120*a* can have a first jackscrew 190*a* with a handle 192 and the right linkage unit 120*b* can have a second jackscrew 190*b* with a handle 192. In operation, the first and second jackscrews 190*a-b* can be rotated to raise or lower the upper crossmember 140*a* to position the support structure 110 in the raised or lowered position, respectively. The embodiment of the positioning apparatus 100 illustrated in FIG. 5 is expected to be particularly useful for use with large, heavy patients.

Figure 6:
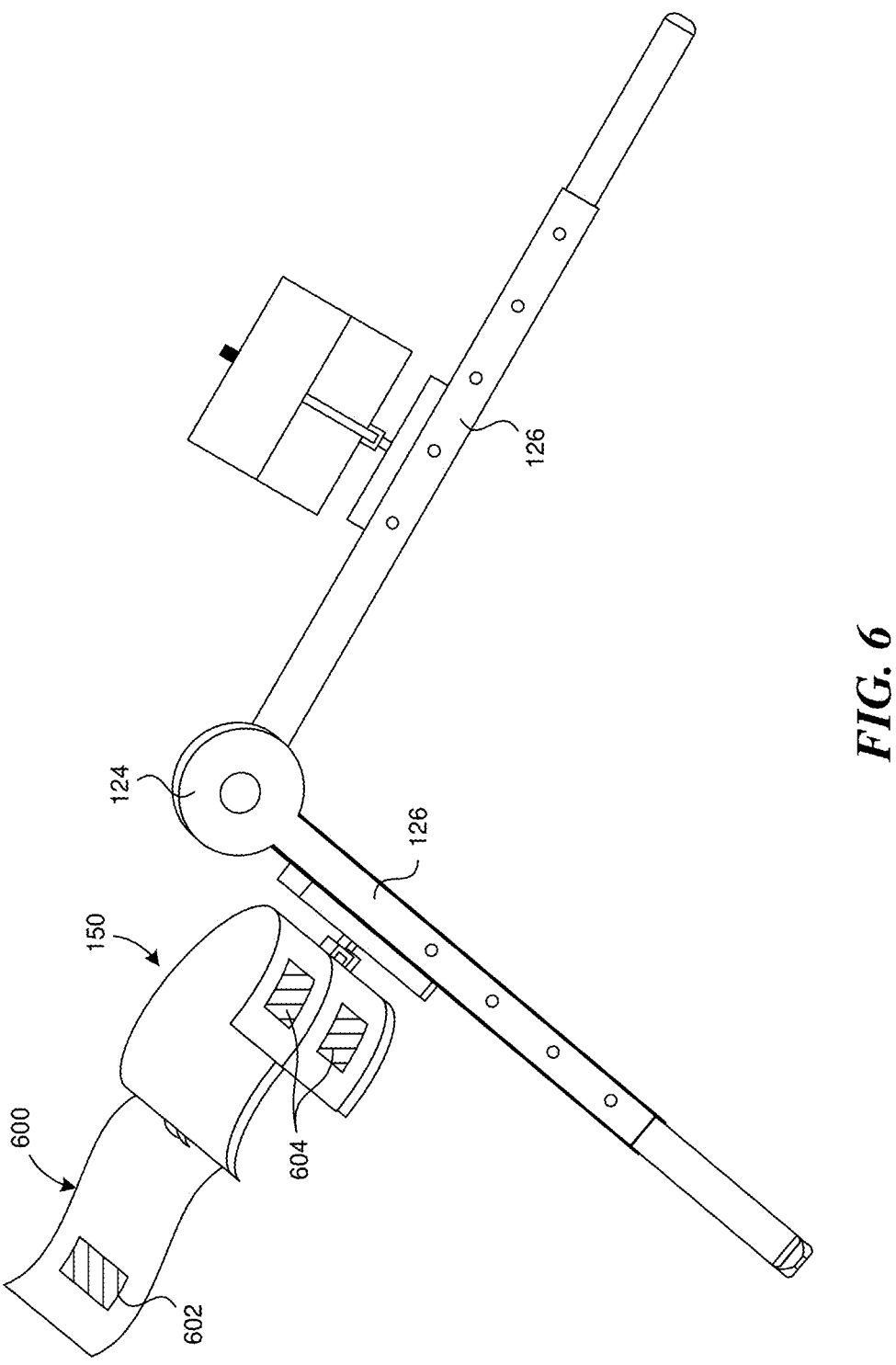
FIG. 6 is an isometric view of a retention element in accordance with the present technology.

FIG. 6 is an isometric view of a retention element 150 in accordance with some embodiments of the present technology. The retention element 150 shown in FIG. 6 has an optional retaining element 600 attached to the holding portion 152. The retaining element 600 can be a strap, belt or other mechanism configured to close the opening 154 of the holding portion 152. Additionally, the retention element 150 can further include fasteners 602 and 604, such as Velcro strips attached to the retaining element 600 and the holding portion 152, respectively. Other types of fasteners and straps can be used as well, such a belts with a holes and buckles, straps with a clamp, etc. The embodiment in FIG. 6 is useful when a patient is quite aggressive such that positioning the retention elements 150 as shown in FIGS. 2D, 4A and 4B do not sufficiently immobilize the patient. As noted above, use of the retaining element 600 is optional and can be prescribed only by a doctor.

From the foregoing, it will be appreciated that specific embodiments of the invention have been described herein for purposes of illustration, but that various modifications may be made without deviating from the scope of the invention. Accordingly, the invention is not limited except as by the appended claims.

I claim:

1. A method of positioning a body part of a patient, comprising:
    placing a body part in at least two retention elements that are mounted to a portable support structure, each retention element comprising a first retention element and a second retention element, each of which having a holding portion and an open region, and each retention element being movable between a receiving position in which the open region faces upward and a retention position in which the open region faces at least partially sideways, wherein the retention elements are in the receiving position when the body part is placed therein;

moving the retention elements into the retention position such that the open regions of the first retention elements face inward and the open regions of the second retention elements face outward; and raising at least a portion of the portable support structure to thereby raise at least a portion of the body part such that the body part is in a desired position for performing a procedure on the patient.

2. The method of claim 1, further comprising moving the retention elements from a medial position laterally outward to a lateral position.

3. The method of claim 1 wherein the procedure comprises a urinary catheterization procedure and wherein:

the portable support structure comprises a left linkage unit, a right linkage unit, and a crossmember having a left connector attached to the left linkage unit and a right connector attached to the right linkage unit;

the retention elements are leg cuffs including a left upper leg cuff and a left lower leg cuff attached to the left linkage unit, and a right upper leg cuff and a right lower leg cuff attached to the right linkage unit; and placing the body part in at least two retention elements comprises placing a left leg in the left upper leg cuff and the left lower leg cuff, and placing a right leg in the right upper leg cuff and the right lower leg cuff.

4. The method of claim 3, further comprising moving the left upper leg cuff such that the open region faces inward, moving the left lower leg cuff such that the open region faces outward, moving the right upper leg cuff such that the open region faces inward, and moving the right lower leg cuff such that the open region faces outward.

5. The method of claim 3, further comprising moving the left upper leg cuff such that the open region faces outward, moving the left lower leg cuff such that the open region faces inward, moving the right upper leg cuff such that the open region faces outward, and moving the right lower leg cuff such that the open region faces inward.

6. The method of claim 3, further comprising moving the left connector of the crossmember laterally outward and moving the right connector of the crossmember laterally outward such that the left upper leg cuff and the right upper leg cuff are spaced further apart from each other.

7. The method of claim 3, further comprising moving the left connector of the crossmember laterally outward and moving the right connector of the crossmember laterally outward such that the left upper leg cuff and the right upper leg cuff are spaced further apart from each other, and wherein raising at least a portion of the support structure comprises raising the crossmember.

8. The method of claim 7 wherein:

the left linkage unit has a first bar, a second bar, and a rotatable joint coupled to the first bar and the second bar;

the right linkage unit has a first bar, a second bar, and a rotatable joint coupled to the first bar and the second bar; and raising at least a portion of the support structure comprises lifting the crossmember and rotating the first bar of the left linkage unit and the second bar of the left linkage unit about the rotatable joint of the left linkage unit and rotating the first bar of the right linkage unit and the second bar of the right linkage unit about the rotatable joint of the right linkage unit.

9. A method of positioning a body part of a patient, comprising:

placing a body part in at least two retention elements that are mounted to a portable support structure, each retention element comprising a first retention element and a second retention element, each of which having a holding portion and an open region, and each retention element being movable between a receiving position and a retention position; and moving the retention elements into the retention position such that the open regions of the first retention elements face a first direction and the open regions of the second retention elements face a second direction different than the first direction.

10. The method of claim 9, further comprising raising at least a portion of the portable support structure to thereby raise at least a portion of the body part such that the body part is in a desired position for performing a procedure on the patient.

11. The method of claim 9 further comprising moving the retention elements from a medial position laterally outward to a lateral position.

12. The method of claim 9, wherein:

each retention element is affixed to the portable support structure at a mount having a retainer, each retention element further includes a connector received in the retainer, and wherein the retention elements are rotatable relative to the mounts such that the connectors slide through the retainers.

13. The method of claim 9, wherein:

the portable support structure comprises a left linkage unit, a right linkage unit, and a crossmember having a left connector attached to the left linkage unit and a right connector attached to the right linkage unit;

the retention elements are leg cuffs including a left upper leg cuff and a left lower leg cuff attached to the left linkage unit, and a right upper leg cuff and a right lower leg cuff attached to the right linkage unit; and placing the body part in at least two retention elements comprises placing a left leg in the left upper leg cuff and the left lower leg cuff, and placing a right leg in the right upper leg cuff and the right lower leg cuff.

14. The method of claim 13, further comprising moving the left upper leg cuff such that the open region faces inward, moving the left lower leg cuff such that the open region faces outward, moving the right upper leg cuff such that the open region faces inward, and moving the right lower leg cuff such that the open region faces outward.

15. The method of claim 13, further comprising moving the left upper leg cuff such that the open region faces outward, moving the left lower leg cuff such that the open region faces inward, moving the right upper leg cuff such that the open region faces outward, and moving the right lower leg cuff such that the open region faces inward.

16. The method of claim 13, further comprising moving the left connector of the crossmember laterally outward and moving the right connector of the crossmember laterally outward such that the left upper leg cuff and the right upper leg cuff are spaced further apart from each other.

17. The method of claim 13, further comprising raising at least a portion of the portable support structure to thereby raise at least a portion of the body part such that the body part is in a desired position for performing a procedure on the patient.

* * * * *